United States Patent [19]

Raman et al.

[11] Patent Number: 5,328,697

[45] Date of Patent: Jul. 12, 1994

[54] COMPOSITIONS AND PROCESSES FOR THE SUSTAINED RELEASE OF DRUGS

[75] Inventors: Siva N. Raman, St. Louis, Mo.; Matthew W. Gray; Rodger L. Smith, both of Terre Haute, Ind.

[73] Assignee: Mallinckrodt Veterinary, Inc., Mundelein, Ill.

[21] Appl. No.: 833,197

[22] Filed: Feb. 10, 1992

[51] Int. Cl.$^5$ .......................... A61K 9/38; A61K 9/42; A61K 37/36

[52] U.S. Cl. .................... 424/477; 424/474; 424/475; 424/476; 424/491; 424/498; 424/495; 424/468; 514/960

[58] Field of Search ............... 424/477, 476, 474, 475, 424/495, 499, 498, 468, 491

[56] References Cited

U.S. PATENT DOCUMENTS

| | | | |
|---|---|---|---|
| 2,921,883 | 1/1960 | Reese et al. | 167/82 |
| 3,119,742 | 1/1964 | Heimlich et al. | 167/82 |
| 3,220,925 | 11/1965 | Schroeter | 167/82 |
| 3,365,365 | 1/1968 | Butler et al. | 167/82 |
| 3,383,283 | 5/1968 | Brindamour | 167/83 |
| 4,415,547 | 11/1983 | Yu et al. | 424/19 |
| 4,524,060 | 6/1985 | Mughal et al. | 424/19 |
| 4,572,833 | 2/1986 | Pedersen et al. | 424/467 |
| 4,600,577 | 7/1986 | Didriksen | 424/20 |
| 4,634,587 | 1/1987 | Hsiao | 424/19 |
| 4,684,516 | 8/1987 | Bhutani | 424/19 |
| 4,695,467 | 9/1987 | Uemura et al. | 424/502 |
| 4,708,867 | 11/1987 | Hsiao | 424/80 |
| 4,806,361 | 2/1989 | Harrison et al. | 424/495 |
| 4,828,840 | 5/1989 | Sakamoto et al. | 424/474 |
| 4,863,736 | 9/1989 | Azain et al. | 424/426 |
| 4,871,549 | 10/1989 | Ueda et al. | 424/495 |
| 4,874,613 | 10/1989 | Hsiao | 424/458 |

FOREIGN PATENT DOCUMENTS 338383 10/1989 European Pat. Off. .
8701588 3/1987 PCT Int'l Appl. .

*Primary Examiner*—Thurman K. Page
*Assistant Examiner*—James M. Spear
*Attorney, Agent, or Firm*—Wendell R. Guffey; Barbara Ernst; Thomas L. Farquer

[57] ABSTRACT

The present invention relates to compositions for the sustained release of drugs and to methods for the production of such compositions. In one embodiment, somatotropin is layered onto non-pareil seeds, which, in turn are sprayed with a glycine solution. Next, a coating of a wax mixture is applied.

3 Claims, 2 Drawing Sheets

COMPOSITIONS AND PROCESSES FOR THE SUSTAINED RELEASE OF DRUGS

BACKGROUND OF THE INVENTION

This invention relates to compositions and processes for the sustained release of drugs. Sustained release compositions or devices for the delayed release of drugs have been used for many years. Such compositions or devices increase the effectiveness of many drugs. Various compositions have been developed, each with a varying degree of success.

For example, the use of drug-containing pellets known as non-pareil seeds has been known since at least 1862. See e.g., U.S. Pat. No. 36,816. Non-pareil seeds are pellets made from sugar and starch. Subsequently, these drug containing pellets came to be coated with a digestible or dispersable delayed release coating. Often, various coatings having different release characteristics would be used on groups of pellets which then would be combined in a single gelatin capsule. As recognized in U.S. Pat. No. 3,119,742, incorporated herein by reference, this procedure had the significant disadvantage of being limited to drugs of relatively small doses.

U.S. Pat. No. 4,871,549, also incorporated herein by reference, discloses one method of preparing a sustained release composition. Pellets incorporating a swelling agent are coated with an outer membrane. The swelling agent absorbs fluid and the outer membrane breaks, releasing the drug quickly from each pellet.

A need exists for new and improved methods and compositions which administer drugs in a sustained fashion. Particularly with respect to proteins such as somatotropins, which are most effective when administered over a period of days or weeks, there is a need for such processes and compositions.

SUMMARY OF THE INVENTION

The present invention relates to compositions and processes for the sustained release of drugs, including proteins. A preferred composition of the present invention includes non-pareil seeds which have been coated with a drug, preferably a protein such as somatotropin, and most preferably porcine somatotropin. The protein coat surrounds the non-pareil seeds. In one embodiment, a primary coating layer, typically a water-soluble agent, surrounds the protein coat. A secondary coating layer, typically wax, surrounds the entire device.

In another embodiment, a tablet containing a drug is coated with a primary coating layer. A secondary coating surrounds the primary coating.

A process for preparing compositions capable of providing sustained release of drugs, including proteins such as somatotropins, also is disclosed. In this process, the drug is coated onto non-pareil seeds. The drug-coated seeds are coated with a solution of a water-soluble agent, such as glycine, to provide a primary-coated seed. The primary-coated seeds then are coated with a secondary coat of a water-insoluble substance such as a wax to provide seeds capable of sustained release of the drug. Optionally, these seeds can be assembled in, for example, gelatin capsules.

DETAILED DESCRIPTION OF THE BEST MODE OF PRACTICING THE INVENTION

Figure 1:
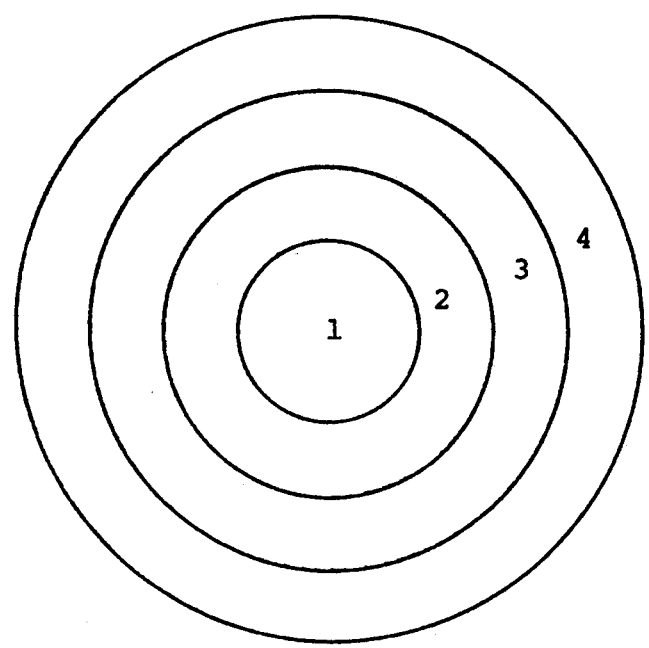
FIG. 1 represents a schematic of a sustained-release composition intended to depict the layering of the elements of the composition. It is not representative of the relative size of any of these layers embodying the present invention.
Figure 2:
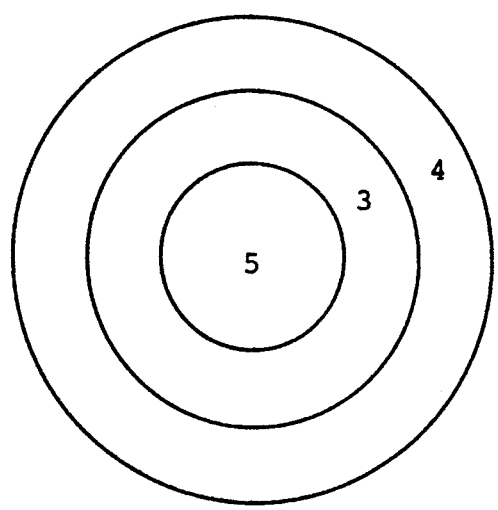
FIG. 2 represents a schematic of an alternative embodiment of a sustained release composition intended to depict the layering of the elements on a drug-containing tablet. It is not representative of the relative size of any of these layers embodying the present invention.

The present invention provides a composition for the sustained release of drugs. The invention can be used with any type of drug requiring a sustained release. As used herein the term "drug" means compounds for the diagnosis, cure, mitigation, treatment or prevention of disease in man or other animals. See Lachman, et al., *Theory and Practice of Industrial Pharmacy*, 3rd Ed. (1986), incorporated herein by reference. For example, drugs such as metoclopramide or metoprolol tartrate can be administered using the present invention. However, proteins are a preferred type of drug for use in this invention. Somatotropin is an especially preferred type of protein. Porcine somatotropin is a most especially preferred somatotropin.

As used herein, somatotropin means a polypeptide, whether natural, synthetic, or recombinant, having a chemical structure and the growth-promoting activity known by those of skill in the art to be typically associated with somatotropin produced in the pituitary gland of an animal. "Somatotropin" includes those natural somatotropins produced by the pituitary or expressed by a genetically engineered microorganism. While somatotropins from all species are included, porcine somatotropin (pST) is a preferred embodiment. A preferred form of pST, Δ7-pST, which has an amino acid sequence corresponding to that of the full-length porcine somatotropin less the first seven amino acids of the mature polypeptide, is specifically contemplated for use in the present invention. Δ7-pST is disclosed in European Patent Application No. 83305717.7, incorporated herein by reference.

In the following description of the invention, unless otherwise stated, somatotropin shall be used as a representative example of the types of substances which are useful in the compositions and processes of the invention. It is to be understood that this use of somatotropin is not to be considered to limit the invention to any particular type or class of active component.

In general, the composition includes non-pareil seeds which have been coated with somatotropin. Both non-pareil seeds and the use thereof are known to those of skill in the art. Typically, and as used in the preferred embodiment of the present invention, non-pareil seeds can be made by any suitable method known to those of skill in the art from a mixture of sucrose and starch, such as from about 1–90% sucrose and from about 10–99% starch, preferably about 70% sucrose and 30% starch. For the purposes of the present invention, the size range of such non-pareil seeds is preferably between about 1 and 2000 microns. Most preferably, seeds between about 700 and 1700 microns are used.

Any desired amount of somatotropin can be coated onto the seeds. Typically, the amount will be a pharmaceutically effective amount. As used herein, "pharmaceutically effective amount" means an amount of drug effective to induce the desired response in an animal. A pharmaceutically effective amount of a drug either is known or readily can be determined, without undue experimentation, by those of skill in the art. For example, without in any way intending to limit the invention and as an illustration only, a pharmaceutically effective amount of porcine somatotropin is from about 24 grams to about 120 grams of porcine somatotropin per kilogram of seeds. The desired amount of somatotropin can be dissolved or suspended in water. Effective amounts of desired excipients, such as stabilizers or solubilizers, can be included. A typical stabilizer can be sucrose, while a typical solubilizer can be EDTA. The somatotropin solution or suspension can be applied to the seeds using a fluidized bed coater or other suitable method. Such methods are known to those of skill in this art. Application of the somatotropin solution or suspension is continued until the seeds are coated with the desired amount of somatotropin. The bed temperature can vary but generally ranges from about 37° to 45° C. As a result of this step, a somatotropin-coated seed is formed.

The somatotropin-coated seeds are coated with a primary coating layer. As used herein, "primary coating layer" refers to the coating of material directly adjacent and external to the somatotropin layer or, as discussed below, to the tablet. As used herein, "the primary coating layer" is defined to include a water-soluble agent, such as glycine, either alone or in combination with another water-soluble agent, preferably in an aqueous solution. Glycine is a preferred material for this purpose. Other materials, without limitation, which can be used include alanine, arginine, and tartaric acid. Other water-soluble agents can also be used. For illustrative purposes, throughout this disclosure, glycine will be used as representative of this material.

An aqueous solution of glycine can be applied to the coated seeds using a fluidized bed coater. The use of fluidized bed coaters is known to those of ordinary skill in the art. The amount of glycine in solution can vary, but typically ranges from about 2% to the saturation concentration, i.e., about 25%, and is preferably from about 5% to about 20%, most preferably about 15% by weight. Optionally, the glycine solution can contain a binder, such as polyvinylpyrrolidone, to produce a more uniform, tough coating. Any desired amount of glycine can be applied. Typically, amounts of from about 5% to about 20% by weight are applied. Most preferably, glycine is sprayed onto the seed until it accounts for about 10% of the seed's weight. Percentage is determined as follows:

$$\frac{[\text{weight of the primary coating material}] \times 100}{[\text{weight of the primary coating material}] + [\text{weight of the somatotropin coated seed}]}$$

This step results in the formation of a glycine-coated somatotropin-seed.

The glycine-coated somatotropin-coated seeds desirably are coated with a secondary coating layer. As used herein, "secondary coating layer" means the layer adjacent and external to the primary coating layer, which coats the entire device. Typically, the secondary coating layer comprises a water-insoluble material so as to provide delayed release of the drug. Such materials are known to those of skill in the art and include waxes and polymeric coatings such as ethyl cellulose or acrylic polymers, for example. For implant applications, a wax mixture is especially preferred. As used herein, a "wax mixture" shall include at least one type of wax. Any desirable ratio of waxes can be selected. For example, one such desirable ratio is about 80% STEARINE® (partially hydrogenated cottonseed oil) to about 20% beeswax. An especially preferred mixture is about 70% STEARINE® and about 30% beeswax. Optionally, an amount of nonionic surfactant can be added. Suitable surfactants are known to those of skill in the art and include ethoxylated mono- and di-glycerides, such as MAZOL® 80 MGK and the like. The amount can range from about 0.01% to about 20% by weight of the secondary coating layer, and preferably is from about 0.02% to about 2%. Other suitable, optional additives for the secondary coating layer include polypropylene glycol or polyethylene glycol and the like. The mixture of waxes, including any desired additives, is melted and can be applied to the coated seeds using a fluidized bed coater. The percent of the secondary coating layer can range from about 2% to 50%, preferably from about 5% to 30% of the total weight of the non-pareil seed and all the above-described coatings. The thickness and composition of the secondary coating layer can be altered as desired to obtain particular release profiles.

Unexpectedly, the present inventors have found that the interpolation of the primary coating layer between the drug coating or tablet and the secondary coating layer results in a prolonged delay of the rupture of the secondary coating and the subsequent release of drug. This delay is completely surprising given the teaching of the prior art that the use of glycine or another osmotic agent would result in swelling upon contact with water, thereby causing a premature rupture of the secondary coating layer with a concurrent early release of drug.

An embodiment of the present invention is illustrated in FIG. 1. Non-pareil seeds 1 are coated with a drug 2. The drug coating underlies a coating of the primary coating layer 3. The entire device is coated with the secondary coating layer 4. Typically, the drug coating 2 is adjacent to, permeating and adhering to the non-pareil seed 1. The primary coating layer 3 surrounds and adheres to the drug coating 2. The secondary coating layer 4 surrounds and adheres to the primary coating layer 3.

In an alternative embodiment, as depicted in FIG. 2, a drug-containing tablet 5 is coated with a primary coating layer 3 and a secondary coating layer 4. The tablet can be made using procedures known in the art. For instance, as illustrated in example 7 below, the drug can be mixed with one or more conventional bases, fillers and/or excipients, then granulated and pressed into tablets. Alternatively, the tablet can be formed by combining non-pareil seeds with a drug. Seeds coated with a drug can be used to form the tablet, or uncoated seeds can be pulverized and combined with a drug during the tableting procedure. In both instances, standard tableting procedures are used. Techniques for forming tablets are well known and are not a part of this invention. After the tablet is formed, it can be coated with a primary coating layer 3, which surrounds and adheres to the entire tablet. A secondary coating layer 4, surrounds and adheres to the primary coating layer.

The primary-layer coated seeds or tablet form what is defined herein as the "core" of the composition. Preferably, the core of the composition contains at least about 40% water-soluble materials.

Seeds or tablets, which have been successively coated as described herein, can be used singly or in combination in various types of implant, oral, or parenteral forms of administration known to those of skill in the art. Alternatively, seeds having varying amounts of the primary and secondary coatings can be combined in a water-soluble capsule for administration. Utilizing seeds having varying amounts of coatings in a single capsule permits an even greater release period to be selected. Suitable water-soluble capsules include gelatin, polyvinylpyrrolidone, hydroxypropyl cellulose or other capsules known to those of skill in the art. In one embodiment, such seeds can be used to promote growth in animals. Typically, growth-promoting amounts of somatotropin, which amounts readily can be determined by those of skill in the art, are administered to an animal by any suitable means of administration such as, for example, those means described herein.

The present invention having been generally described, the following non-limiting examples are set forth for illustrative purposes.

EXAMPLES

Example 1

Porcine serum albumin (PSA) (200 g; obtained from Miles Laboratories, Elkhart, Ind.) was dissolved in 1800 ml sterile water (obtained from Abbott Laboratories). This solution was sprayed at a rate of 8 g/min onto 963 grams of non-pareil seeds (size: 1400–1700 microns) using a Glatt GPCG-1 fluid-bed coater. The coater was fitted with a Wurster column insert, with a partition height of 15 mm. The inlet air temperature was set at 65° C. The product bed temperature was about 38° to 43° C. and the atomizing air pressure was maintained at about 3 Bar. The process efficiency was about 50%. The resulting non-pareil seeds layered with PSA are referred to as "PSA-seeds" in the following examples. The percent PSA loading was determined by extracting PSA from 200 mg of PSA-seeds with 8 ml Phosphate buffered saline (PBS, pH: 7.4) and analyzing the solution by UV/Vis spectrometry. The loading was found to be 11.2±0.16% by weight.

Example 2

PSA-seeds prepared as in Example 1 were coated with wax. To conserve on PSA-seeds, dyed non-pareil seeds were used as filler seeds. PSA-seeds (100 g) were mixed with 1.4 kg of filler seeds and placed in the coater. A mixture of STEARINE ® wax (70 parts by weight), beeswax (30 parts), and 0.1 part MAZOL ® 80 MGK (a surfactant) was melted and sprayed onto the seeds using the machine configuration mentioned in Example 1 above. The process parameters are listed in Table 1. This example represents a control system.

The process efficiency was 93% and the percent wax coating was determined to be 24.8%±0.5% by weight. In vitro release of the PSA was monitored using UV spectrometry, and about 94% of the protein was released in 1 hour.

TABLE 1

| Parameters for Wax Coating | |
|---|---|
| Wax Temperature | 133° C. |
| Atomization Air Temperature | 105° C. |
| Inlet Air Temperature | 42° C. |
| Product Bed Temperature | 42° C. |
| Spray Rate | 7 (g/min) |
| Atomizing Air Pressure | 1.5 Bar |

Example 3

PSA-seeds (about 100 g) prepared as in Example 1 were fluidized with 1 kg of non-pareil seeds (fillers) in the Glatt GPCG-1 coater and sprayed with a 15% aqueous solution of glycine containing 1% polyvinylpyrrolidone. The spray-rate was 6 g/min. The inlet air temperature was 66° C. and the product bed temperature, 49° C. The percent glycine was estimated to be about 9.7% by weight. The process efficiency was 65%. The resulting product ("PSA-glycine-seeds") then was coated with wax as described in Example 2 to give a wax coating weight of 28.2±0.7%. The process efficiency was 96%. The resulting product was termed "PSA-glycine-wax seeds." The in vitro release profile of the PSA-glycine-wax seeds was determined as follows: Two hundred milligrams of the PSA-glycine-wax seeds were placed in each of 5 culture tubes containing 5 ml of PBS at PH 7.4. The tubes were shaken in a water-bath at 37° C. Periodically, the buffer solutions were decanted for UV analysis and replaced with fresh PBS. The absorbance at 278 nm was used to measure the protein concentration. The cumulative amount of the protein released is given in Table 2. Comparing the release profiles of samples from Examples 2 and 3, it is apparent that the release of the protein was delayed more in the case of the PSA-glycine-wax seeds than the PSA-wax seeds.

TABLE 2

| Release Profile for PSA-glycine-wax seeds. | |
|---|---|
| Time (hours) | Cumulative Percent Released |
| 1 | 38.4 ± 4.2 |
| 2 | 69.7 ± 5.8 |
| 4 | 79.4 ± 7.0 |
| 8 | 90.5 ± 6.6 |
| 19 | 98.0 ± 5.5 |
| 33 | 99.2 ± 6.3 |

Example 4

An aqueous suspension (1727 g) containing zinc-complexed rpST (Zn-rpST) (about 24 g) made in accordance with the method disclosed in European Patent Application 0277043, incorporated herein by reference and polyvinylpyrrolidone (4.7 g) was layered onto non-pareil seeds (1 kg; 1400–1700 microns) as in Example 1. Inlet air temperature was maintained at 55° C. and the product bed temperature at 40° C. during the layering process. The spray-rate was about 8–10 g/minute. At the end of the run, 1000 g of seeds containing pST ("pST-seeds") were obtained. The process efficiency was 87%. The pST-seeds (950 g) were layered further with an aqueous suspension (5492 g) containing Zn-rpST (about 96 g) and PVP (9.6 g). The process efficiency was about 79%. It is to be understood that the furthering layering was optional.

Example 5

One hundred grams of pST-seeds prepared as in Example 4 were mixed with non-pareil seeds (900 g; used as fillers) in Glatt GPCG-1 fluid-bed coater and coated with wax (STEARINE ®/beeswax/MAZOL ® 70/30/0.1 parts by wt.). The amount of wax applied was 230 g and the wax coating weight was determined to be 17.0±0.2%. Release of pST from the "pST-wax seeds" was determined as described in Example 3. The results are presented in Table 3 below. Example 5 represents a control system.

Example 6

Fifty grams of pST-seeds prepared as in Example 4 were mixed with 950 g non-pareil seeds (fillers) and layered with an aqueous solution of glycine. The aqueous solution of glycine was prepared by dissolving 300 g of glycine and 20.1 g of PVP in 2 kg DI water. When the layering was complete, a total of 1319 g of product ("pST-glycine seeds") was recovered. The pST-glycine seeds were separated from the filler seeds.

Wax coating of the pST-glycine seeds was carried out by mixing 60 g of the pST-glycine seeds with 1 kg of filler seeds and spray-coating the mixture with wax. The wax composition was STEARINE ®/beeswax/- MAZOL ®/70/30/0.1 parts by wt. and the amount of wax applied was 230 g. The wax coating weight on the seeds was determined to be 14.2±0.4%. Release of pST from the "pST-glycine-wax-seeds" was determined as in Example 3. The results are shown in Table 3. The release of pST is slower when the primary coating layer of glycine is present.

TABLE 3

Release data for samples from Examples 5 & 6.
(ND indicates no data.)

| Time (hrs) | Cumulative percent released | |
|---|---|---|
| | Example 5 | Example 6 |
| 1 | 38.0 ± 5.9 | 1.8 ± 1.4 |
| 2 | 63.8 ± 8.4 | 8.1 ± 2.6 |
| 4.3 | 77.8 ± 6.8 | 22.6 ± 3.6 |
| 8 | 81.7 ± 5.6 | 30.3 ± 3.0 |
| 24 | 84.2 ± 5.1 | 39.1 ± 3.8 |
| 32 | 84.7 ± 5.1 | 43.0 ± 4.5 |
| 48 | 85.2 ± 5.0 | 64.5 ± 4.0 |
| 56 | ND | 74.5 ± 4.1 |
| 72 | ND | 83.8 ± 2.6 |
| 96 | ND | 88.5 ± 2.1 |

Example 7

A mixture of Zn-rpST, arginine, sucrose, and carboxymethyl cellulose (CMC; sodium salt) was granulated with water and dried to give granules with the final composition of 20/37/37/6 parts by weight (pST/arginine/sucrose/CMC). The powder was then mixed with magnesium stearate and compressed in a B-2 Stokes tablet press. The tablets had a diameter of about 2.3 mm and a mean weight of about 10 mg.

Twenty grams of the tablets were mixed with 1 kg of non-pareil seeds (dia. 1.7–2.0 mm) in a Glatt-GPCG-1 fluid-bed coater and spray-coated with a wax composition of STEARINE ®/beeswax/MAZOL ® (80/20/1 parts by weight). The seeds are used to fill the bed of the fluid-bed coater. The wax coating weight was determined to be about 14% by weight.

Thirty (30) tablets were randomly selected from the batch of about 20 g of wax-coated tablets. Each of the 30 tablets was placed in a culture tube filled with 4 ml of PBS. The tubes were shaken in a water-bath at 37° C. The integrity of the coatings was monitored by examining the coated tablets periodically (every 1–2 hours initially and approximately every 4 hours thereafter). The rupture time was determined by taking the average of the observation time prior to the rupture and the time when the rupture was first noted. From the data, it is possible to calculate the 25th, 50th, and 75th percentile values for the rupture times of the group of coated tablets. The 25th percentile value represents the time by which 25% of the tablets had ruptured. This example illustrates a control. These results are provided in Table 4.

Example 8

Tablets prepared as in Example 7 were used for layering with glycine. An aqueous solution of glycine was prepared by dissolving glycine and PVP in DI water. Twenty grams of tablets were fluidized along with 1 kg of non-pareil seeds (dia. 1.7–2.0 mm) in a Glatt GPCG-1 coater. The glycine solution was sprayed onto the mixture of tablets and seeds to give the glycine content of about 8% by weight. The glycine-layered tablets and non-pareil seeds (fillers) were then coated with STEARINE ®/beeswax/MAZOL ® (80/20/1 parts by weight) to give a wax coating weight of 14%. Rupture profiles were determined as in Example 7 for 30 wax-coated tablets selected randomly from this batch. The data are reported in Table 4.

Example 9

A mixture of Zn-rpST, arginine, sucrose, and polyvinylpyrrolidone (PVP) was granulated with water and dried to give granules of composition 31/31/31/6 parts by weight, respectively. The granules were blended with magnesium stearate and compressed to give tablets with a diameter of about 2.3 mm and a weight of about 10 mg.

Four grams of the tablets were mixed with 1 kg of non-pareil seeds (as a filler) in a Glatt GPCG-1 fluid-bed coater and sprayed with wax. The wax mixture had the composition STEARINE ®/beeswax/MAZOL ® (70/30/0.1 by weight). The wax coating weight was about 15%. This example represents a control. Rupture profile of 30 tablets was determined as in Example 7 and the data are reported in Table 4.

Example 10

Tablets prepared as in Example 9 were layered with glycine. The procedure followed was similar to that of Example 8. The glycine-layered tablets then were coated with a wax mixture as in Example 9. The wax coating weight was about 15%. The rupture profile of 30 tablets thus coated was determined as in Example 7 and the data are reported in Table 4.

Example 11

L-Alanine was layered onto tablets prepared as in Example 9. Layering was in accordance with the procedure set forth in Example 8. Subsequently, the tablets were coated with wax as in Example 9. The rupture profile of 30 tablets was then determined as in Example 7 and the data are reported in Table 4.

Example 12

The procedure in Example 8 was followed to layer L-tartaric acid onto tablets prepared as in Example 9. Subsequently, they were coated with wax as in Example 9. The rupture profile of 30 tablets was determined and the data are reported in Table 4.

Example 13

The procedure set forth in Example 8 was followed to layer sucrose onto tablets prepared as in Example 9. Subsequently, the tablets were coated with wax as in Example 9. The rupture profile of 30 tablets was determined and the data are reported in Table 4.

TABLE 4

Rupture time data for Examples 7-13.

| Example | Percentile Rupture Time (hours) | | |
|---|---|---|---|
| | 25th | 50th | 75th |
| 7 | 5.9 | 9.5 | 9.5 |
| 8 | 25.0 | 31.2 | 42.5 |
| 9 | 2.5 | 3.5 | 5.5 |
| 10 | 3.5 | 18.5 | 43.0 |
| 11 | 11.0 | 26.2 | 54.5 |
| 12 | 6.5 | 10.5 | 19.0 |
| 13 | 5.5 | 7.5 | 10.5 |

The data in Table 4 indicate that the presence of the primary coating layer delays the release of the protein. Tablets containing somatotropin and coated with wax alone, without a primary coating layer, took only 9.5 hours to achieve a 75% rupture rate. When a primary layer of glycine was applied to these tablets, as in Example 8, it took 42.5 hours to achieve a 75% rupture rate.

Example 14

Non-pareil seeds (~72% sucrose and ~28% starch), purchased from Paular Corporation, N.J., were ground and sieved to <150 microns. The powder then was mixed with metoclopramide and sodium carboxymethyl cellulose. The mixture was granulated with water and dried to give granules with the final composition of (metoclopramide/sucrose/starch/CMC) 20/53/21/6 parts by weight. The granules were mixed with 1% magnesium stearate and compressed in a Stokes B-2 tablet press using 2.3 mm (dia.) concave punches. The metoclopramide tablets had a mean weight of about 11 mg. Ten grams of metoclopramide tablets were mixed with 1 kg of non-pareil seeds (dia. 1.7–2.0 mm) and coated with wax as in Example 7. The composition of the wax mixture was STEARINE®/beeswax/MAZOL® (80/20/1 parts by weight). The wax-coating weight was determined to be about 14% by weight. This example represents a control. Rupture profiles for the coated tablets were determined as in Example 7. The data are reported in Table 5.

Example 15

Ten grams of metoclopramide tablets were mixed with 1 kg of non-pareil seeds (dia. 1.0–1.2 mm) in a Glatt GPCG-1 coater. Using the procedure in Example 8, an aqueous solution of glycine was applied to achieve a glycine content of about 8% by weight. This glycine layered mixture of tablets and non-pareil seeds was then coated with wax using the same composition and procedure as in Example 14. The wax-coating weight was determined to be about 14% by weight. Rupture profiles for the coated tablets were determined as in Example 7. The data are reported in Table 5.

Example 16

The procedure in Example 15 was repeated except that L-tartaric acid was used instead of glycine. The amount of tartaric acid layered was about 10% by weight. The wax-coating weight was about 14%. The rupture-time data are reported in Table 5.

Example 17

Metoprolol tartrate salt was granulated with powdered non-pareil seeds, and CMC using the same procedure as for the metoclopramide tablets in Example 14. The composition of the tablet matrix was: metoprolol tartrate/sucrose/starch/CMC 20/53/21/6 parts by weight. Five grams of the metoprolol tartrate tablets were coated with the same wax mixture and procedure as in Example 14. This example represents a control. Rupture profiles were determined as in Example 7. The data are reported in Table 5.

Example 18

Five grams of metoprolol tartrate tablets were layered with glycine and subsequently coated with wax as described in Example 15. The wax coating weight was determined to be about 14%. Rupture profiles were determined as in Example 7. The data are reported in Table 5.

Example 19

The procedure in Example 16 was used to layer L-tartaric acid on metoprolol tartrate tablets and further coat them with wax. The wax coating weight was about 14% and the amount of tartaric acid layered was about 10%. The rupture-time data are reported in Table 5.

TABLE 5

Rupture-time data for Examples 14-19

| Example | "Primary Coating" | Percentile Rupture-Time (Hours) | | |
|---|---|---|---|---|
| | | 25th | 50th | 75th |
| 14 | None | 18.0 | 18.0 | 26.0 |
| 15 | Glycine | 41.5 | 41.5 | 44.6 |
| 16 | Tart. acid | 48.5 | 48.5 | 52.5 |
| 17 | None | 18.0 | 18.0 | 18.0 |
| 18 | Glycine | 26.0 | 30.0 | 34.3 |
| 19 | Tart. acid | 40.8 | 48.5 | 57.0 |

As this table indicates, the release of drug was delayed in the presence of glycine and further delayed in the presence of tartaric acid.

We claim:

1. A composition for the sustained release of somatotropin which comprises a tablet comprised of a combination of somatotropin and a suitable excipient, a primary-coating layer comprising glycine and a secondary-coating layer comprising a wax mixture wherein said primary-coating layer is interposed between said tablet and said secondary-coating layer.

2. A composition for the sustained release of porcine somatotropin comprising a non-pareil seed or tablet coated with porcine somatotropin, a layer of glycine and a layer of wax mixture, said layer of glycine being interposed between said porcine somatotropin and said wax mixture.

3. A method of promoting growth in a mammal comprising administering to said mammal a growth promoting amount of the composition of claim 2.

* * * * *